United States Patent [19]

Töpfl

[11] Patent Number: 4,705,865
[45] Date of Patent: Nov. 10, 1987

[54] CATIONIC REACTION PRODUCTS FORMED FROM 1-AMINOALKYL-IMIDAZOLE COMPOUNDS AND EPIHALOHYDRINS

[75] Inventor: Rosemarie Töpfl, Dornach, Switzerland

[73] Assignee: Ciba-Geigy Corporation, Ardsley, N.Y.

[21] Appl. No.: 794,941

[22] Filed: Nov. 4, 1985

[30] Foreign Application Priority Data

Jan. 21, 1985 [CH] Switzerland ............................ 260/85

[51] Int. Cl.$^4$ ........................................... C07D 231/12
[52] U.S. Cl. ....................................... 548/341; 8/189; 548/336
[58] Field of Search ............................... 548/336, 341

[56] References Cited

U.S. PATENT DOCUMENTS

| 2,043,164 | 6/1936 | Gränacher | 548/325 |
| 3,435,049 | 3/1969 | Hoffer | 548/336 |
| 4,035,145 | 7/1977 | Gipp et al. | 8/189 |
| 4,468,228 | 8/1984 | Dvorsky et al. | 548/341 |
| 4,499,282 | 2/1985 | Dvorsky et al. | 548/341 |

Primary Examiner—Henry R. Jiles
Assistant Examiner—Kurt G. Briscoe
Attorney, Agent, or Firm—Edward McC. Roberts; Meredith C. Findlay

[57] ABSTRACT

1-Aminoalkyl-imidazolium compounds which contain in the 3-position and on the terminal amino group fibre-reactive groupings which have been formed by the addition of an epihalohydrin.

These bireactive imidazolium salts are suitable in particular for improving the dye yield and fastness to wet processing of dyeings and printings which have been produced on cellulose fibre materials with anionic dyes, for example with reactive or direct dyes.

8 Claims, No Drawings

CATIONIC REACTION PRODUCTS FORMED FROM 1-AMINOALKYL-IMIDAZOLE COMPOUNDS AND EPIHALOHYDRINS

The present invention relates to cationic reaction products formed from 1-aminoalkylimidazoles and epihalohydrins, to processes for producing them, and to their use for the improvement of colour yield and fastness to wet processing of dyeings or printings produced with anionic dyes on cellulose fibre material.

The cationic reaction products according to the invention are water-soluble 1-aminoalkyl-imidazolium compounds which contain in the 3-position and on the terminal amino group fibre-reactive groupings which have been formed by the addition of an epihalohydrin.

Preferred compounds are those of the formula

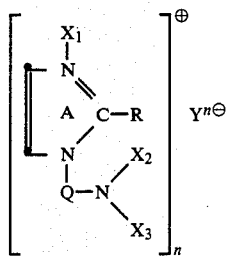   (1)

wherein $X_1$ and $X_2$ independently of one another are each the group

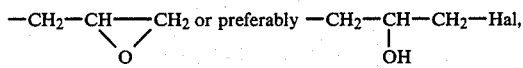

$X_3$ is hydrogen, lower alkyl,

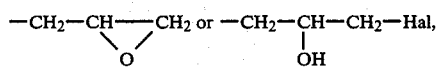

Hal is a halogen atom,
Q is alkylene having 2 to 4 carbon atoms,
R is hydrogen, phenyl or an aliphatic radical,
n is 1 or 2, and
$Y^\ominus$ is an anion of a strong inorganic or organic acid, and wherein the imidazole ring A is unsubstituted, or is substituted by lower alkyl which is unsubstituted or substituted by halogen, hydroxyl or cyano.

Halogen in conjunction with all preceding and following substituents is for example bromine, fluorine, iodine or preferably chlorine.

The fibre-reactive groups $X_1$, $X_2$ and $X_3$ are preferably identical and are in particular

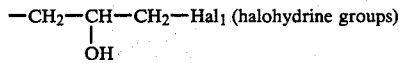 (halohydrine groups)

wherein $Hal_1$ is bromine or preferably chlorine.

The imidazole compound preferably contains two fibre-reactive groupings, namely $X_1$ and $X_2$.

$X_3$ is in particular hydrogen.

The alkylene group Q is for example the —CH$_2$—CH$_2$—, —CH$_2$—CH$_2$—CH$_2$—,

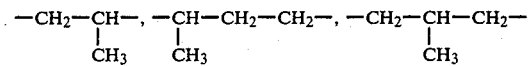

or —CH$_2$—CH$_2$—CH$_2$—CH$_2$— group. Q is preferably the propylene group —CH$_2$—CH$_2$—CH$_2$—.

As an aliphatic radical, R can be saturated or unsaturated, straight-chain or branched-chain, and contain up to 23 carbon atoms. R is advantageously an alkyl group having 1 to 23 carbon atoms.

Examples of such alkyl groups are: methyl, ethyl, n-propyl, isopropyl, n-butyl, isobutyl, n-amyl, isoamyl, hexyl, heptyl, octyl, isooctyl, nonyl, isononyl, undecyl, dodecyl, tridecyl, pentadecyl, heptadecyl, nonadecyl, heneicosyl or tricosyl.

The preferred meaning of R is hydrogen, lower alkyl, undecyl or heptadecyl. Lower alkyl can be substituted by halogen, cyano or hydroxyl.

Lower alkyl is as a rule such groups or parts of groups which contain 1 to 5, especially 1 to 3, carbon atoms, for example methyl, ethyl, n-propyl, isopropyl, n-butyl, isobutyl, tert-butyl, n-amyl, isoamyl or tert-amyl.

If eventual lower alkyl groups are substituted, they are in particular haloalkyl, cyanoalkyl or hydroxyalkyl which in each case contain 2 to 4 carbon atoms, for example 2-chloroethyl, 2-cycloethyl, 2-hydroxyethyl or 3-hydroxypropyl.

Preferred substituents of the ring A are methyl and ethyl.

Anions $Y^\ominus$ are both anions of inorganic acids, such as the chloride, bromide, fluoride, iodide, sulfate or phosphate ion, and anions of organic acids, for example: aromatic or aliphatic sulfonic acids, such as the benzenesulfonate, p-toluenesulfonate, chlorobenzenesulfonate, methane- or ethanesulfonate ion; also the anions of lower carboxylic acids, for example the acetate, propionate or oxalate ion.

$Y^\ominus$ is especially the chloride, bromide or sulfate ion.

Important cationic fibre-reactive compounds in practice correspond to the formula

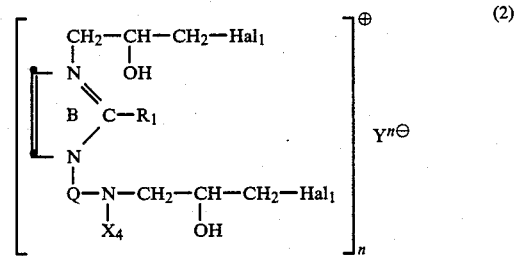 (2)

wherein $Hal_1$, Q, $Y^\ominus$ and n have the meanings defined above,
$R_1$ is hydrogen, phenyl or alkyl having 1 to 17 carbon atoms, and
$X_4$ is hydrogen or

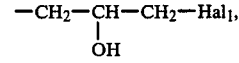

and the ring B is unsubstituted or substituted by methyl or ethyl.

More especially of interest are imidazolium compounds of the formula

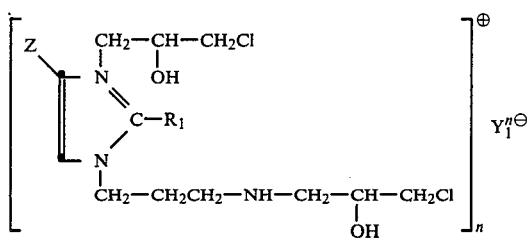

wherein
$R_1$ is hydrogen, phenyl or alkyl having 1 to 17 carbon atoms,
Z is hydrogen or methyl,
n is 1 or 2, and
$Y_1^{n\ominus}$ is the chloride or sulfate ion.

Preferred among the imidazolium compounds of the formulae (2) and (3) are those in which $R_1$ is hydrogen or $C_1-C_{17}$-alkyl.

Typical representatives of the imidazolium compounds according to the invention are:
1-[3'-chloro-2'-hydroxypropylamino-propyl]-3-(3'-chloro-2'-hydroxypropyl)-imidazolium chloride,
1-[di-(3'-chloro-2'-hydroxypropyl)amino-propyl]-3-(3'-chloro-2'-hydroxypropyl)-imidazolium chloride,
1-[3'-chloro-2'-hydroxypropylamino-propyl]-3-(3'-chloro-2'-hydroxypropyl)-imidazolium sulfate,
1-[di-(3'-chloro-2'-hydroxypropyl)-amino-propyl]-3-(3'-chloro-2'-hydroxypropyl)-imidazolium sulfate,
1-(3'-chloro-2'-hydroxypropylamino-propyl)-3-(3'-chloro-2'-hydroxypropyl)-2-methyl-imidazolium sulfate,
1-(3'-chloro-2'-hydroxypropylamino-propyl)-3-(3'-chloro-2'-hydroxypropyl)-2-undecyl-imidazolium sulfate,
1-(3'-chloro-2'-hydroxypropylamino-propyl)-3-(3'-chloro-2'-hydroxypropyl)-2-heptadecyl-imidazolium sulfate, and
1-(3'-chloro-2'-hydroxypropylamino-propyl)-3-(3'-chloro-2'-hydroxypropyl)-2-phenyl-imidazolium sulfate.

The imidazolium salts are produced in a manner known per se. They are preferably produced by reacting 1 mol of a corresponding 1-substituted imidazole compound, or preferably the acid salt thereof, for example with hydrochloric acid or sulfuric acid, with 2 or 3 mols of an epihalohydrin, such as epibromohydrin, β-methylepichlorohydrin or preferably epichlorohydrin.

The reaction conditions for producing the imidazolium salts are to be selected in a manner ensuring that neither as a result of too high a pH value of the reaction medium nor as a result of too high a temperature does a premature exchange of mobile substituents occur. The reaction is performed therefore preferably in a dilute aqueous medium under conditions as mild as possible with respect to temperature and pH-value, advantageously at a temperature of 30° to 95° C. and at a pH-value of 5 to 8, preferably 5.5 to 7, and to obtain the desired pH-value a hydrohalic acid, for example hydrochloric acid or sulfuric acid, can be added.

Suitable imidazole components for obtaining the imidazolium salts according to the invention are for example: 1-aminoethylimidazole, 1-aminopropylimidazole, 1-aminobutylimidazole, 1-aminopropyl-2-methylimidazole, 1-aminopropyl-2-isopropylimidazole, 1-aminopropyl-2,4-dimethylimidazole, 1-aminopropyl-4-methylimidazole, 1-aminopropyl-2-phenylimidazole, 1-aminopropyl-2-heptylimidazole, 1-aminopropyl-2-undecylimidazole, 1-aminopropyl-4-methyl-2-ethylimidazole, 1-aminopropyl-4,5-dimethyl-2-undecylimidazole, 1-aminopropyl-4-ethyl-2-undecylimidazole, 1-aminopropyl-2-heptadecylimidazole, and the corresponding acid salts.

1-Aminopropyl-2-methylimidazole, 1-aminopropyl-2-phenylimidazole, 1-aminopropyl-2-heptadecylimidazole and in particular 1-aminopropylimidazole are especially preferred.

Imidazolium salts according to the invention are particularly suitable for improving the dye yield and fastness to wet processing of dyeings or printings which are produced on cellulose fibre materials with anionic dyes.

The treatment of the cellulose fibre material with the cationic imidazole compound is preferably performed continuously by a pad dyeing process. The cellulose fibre material is impregnated with the fixing agent, for example by slop-padding, and is then subjected to a fixing process. This application can be carried out before dyeing, during dyeing or after dyeing. The treatment after dyeing is preferred. The aftertreatment can be performed both on dyeings and on colour printings.

The impregnating stage can be undertaken at 20° to 70° C., preferably however at room temperature. The fixing stage can be carried out by a steaming process, a thermosol process, a microwave treatment or a hot dwell or cold pad batch process.

In the case of the steaming process, the textile materials padded with the treatment liquor are subjected to a fixing treatment in a steamer with optionally superheated steam, advantageously at a temperature of 98° to 130° C., preferably at 102°–110° C.

Fixing by the so-called thermosol process can be performed, after or without intermediate drying, for example at a temperature of 100° to 210° C. The thermosol fixation is preferably carried out at a temperature of 120° to 210° C., especially at 140° to 180° C. and after an intermediate drying at 80° to 120° C. of the padded or printed material. Depending on the temperature, thermosol fixing can take 20 seconds to 5 minutes, preferably 30 to 180 seconds.

Thermofixing can also be effected by the use of microwaves. For this purpose the material, after impregnation with the treatment liquor and squeezing out of the excess moisture, is advantageously rolled up, and then treated in a chamber by means of microwaves. This microwave treatment can take 2 to 120 minutes, 2 to 15 minutes being preferably sufficient. Microwaves are designated as being electromagnetic waves (radio waves) in the frequency range of 300 to 100,000 mHz, preferably 1000 to 30,000 mHz.

In the hot dwell process, the padded or printed material is left in the moist condition, for example for 15 to 120 minutes, advantageously at a temperature of 85° to 102° C. The impregnated material can be preheated by an infrared treatment to 85° to 102° C. The dwell temperature is preferably 90° to 100° C.

The fixing stage can be performed also according to the cold pad batch process by storage of the padded or printed and preferably rolled up material at room temperature (15° to 30° C.) for example for 3 to 24 hours. Storage can optionally be carried out also at a slightly elevated temperature (30° to 80° C.).

The continuous treatment after dyeing is preferably carried out by padding of the dyed or printed fibre material with the subsequent thermosol process.

The treatment of the textile materials with the imidazolium salts can be performed also in the exhaust process, before, during or after dyeing, particularly however before or after dyeing. The treatment in this case can be carried out at temperatures in the range of 20° to 135° C., preferably 40° to 100° C. The ratio of goods to liquor can be selected within a wide range, for example 1:2.5 to 1:100, preferably 1:5 to 1:40.

The treatment liquors contain the imidazolium salts in the exhaust process preferably in an amount of 0.1 to 25% by weight, especially 2 to 15% by weight, relative to the weight of the cellulose fibre material, or in the case of padding liquors or printing pastes preferably in an amount of 1 to 100 g/liter, most preferably 10 to 50 g/liter, the squeezing effect in the padding process being advantageously 60 to 120% by weight.

The dyes used are the substantive dyes, or in particular reactive dyes, customarily employed for dyeing cellulose textile materials.

Suitable substantive dyes are the usual direct dyes, for example the Direct Dyes mentioned in Colour Index, 3rd Edition (1971), Vol. 2, on pages 2005-2478.

By reactive dyes are meant the customary dyes which form a chemical bond with the cellulose, for example the Reactive Dyes listed in Colour Index, Vol. 3 (3rd Edition, 1971) on pages 3391-3560, and in Vol. 6 (revised 3rd Edition, 1975) on pages 6268-6345.

With simultaneous dyeing and treatment with the imidazolium salts, the amount of dye is determined as a rule by the desired colouring strength, and in the continuous process is advantageously 0.1 to 100 g per liter of liquor, preferably 5 to 60 g per liter of liquor. In the exhaust process, the amount of dye is advantageously 0.1 to 10% by weight, preferably 1 to 6% by weight.

In addition to the cationic imidazolium salts, the liquors contain alkaline reacting compounds, for example: sodium carbonate, sodium bicarbonate, sodium hydroxide, disodium phosphate, trisodium phosphate, borax, aqueous ammonia or alkali donors, for example sodium trichloroacetate or sodium formiate. The applied amount of alkalies with respect to alkali metal hydroxides is preferably 3 to 9 g per liter of liquor, and with respect to alkali metal carbonates preferably 8 to 25 g per liter of liquor.

The pH-value of the treatment liquors or dye liquors is as a rule 8 to 13.5, preferably 9.5 to 13.

The liquors if desired can also contain urea, glycerol, sodium formiate, electrolytes, for example sodium chloride or sodium sulfate, alkali-resistant wetting agents, homopolymers or copolymers of acrylamide or methacrylamide, or graft polymers, such as those described in European published patent application EP-A 111454, as well as thickening agents, for example alginates, starch ethers or carob seed grain ethers.

The imidazolium salts according to the invention are suitable for the treatment of textiles consisting of cellulose or containing cellulose.

Applicable cellulose fibre material is that formed from regenerated or in particular natural cellulose, for example staple fibre, viscose silk, cellulose acetate, hemp, linen, jute or preferably cotton; and also mixtures of fibres, for example those consisting of polyamide and cotton, or especially of polyester and cotton, the polyester constituent being able to be preliminarily dyed or subsequently dyed.

The textile material can be in any desired form, for example in the form of yarn, hanks of yarn, fabrics and knitted goods, felt, preferably in the form of textile sheet materials, such as fabrics or looped fabrics, which consist completely or partially of native, regenerated or modified cellulose.

With the use of the imidazolium salts according to the present invention, there are obtain level and deeply coloured dyeings which, compared with those obtained by hitherto known processes, are distinguished by an improved dye yield. In particular, there are produced with reactive and also with substantive dyes, on cellulose fibre material, dyeings and printings which exhibit a considerable improvement with respect to fastness to wet processing. Furthermore, the tensile strength of the dyeings is not impaired by the use of the imidazolium salts as defined herein. Depending on the amounts applied, these imidazolium salts can impart to the cellulose fibre material simultaneously resistance to creasing and resistance to shrinking, instead of these properties having to be imparted by additional corresponding finishing agents.

Except where otherwise stated in the following Examples, percentage values relate to weight. The amounts in the case of the dyes apply to commercial products, that is to say, to diluted products, and in the case of the auxiliaries to pure substances. The five-digital Colour-Index numbers (C.I.) are with reference to the 3rd. Edition of the Colour Index.

PRODUCTION EXAMPLES

EXAMPLE 1

37.5 g of 1-(3-aminopropyl)-imidazole are dissolved in 78 g of water and 15.3 g of sulfuric acid (96%), whereupon the temperature rises to 60° C. To this solution are then added dropwise 55.5 g of epichlorohydrin in the course of 60 minutes, during which time the temperature is held between 60° and 66° C. After completion of the dropwise addition, the reaction mixture is stirred at 65° C. for a further 2 hours. After this time, the epoxide content is zero. The solution obtained is evaporated to dryness to thus obtain 106 g of 1-(3'-chloro-2'-hydroxypropylaminopropyl)-3-(3'-chloro-2'-hydroxypropyl)-imidazolium sulfate.

EXAMPLE 2

42.84 g of 1-(3-aminopropyl)-2-methylimidazole are dissolved in 83 g of water and 15.3 g of 96% sulfuric acid, whereupon the temperature rises to 59° C. To this solution are then added dropwise 55.5 g of epichlorohydrin in the course of 40 minutes, the temperature during this time being held between 65° and 70° C. After the dropwise addition has been completed, the reaction mixture is stirred at 65° C. for a further 2½ hours. The epoxide content after this time is zero. The reaction mixture is evaporated to dryness to thus leave 113 g of 1-(3'-chloro-2'-hydroxypropylaminopropyl)-3-(3'-chloro-2'-hydroxypropyl)-2-methylimidazolium sulfate.

EXAMPLE 3

66.9 g of 1-(3-aminopropyl)-2-phenylimidazole are dissolved in 107 g of water and 15.3 g of 96% sulfuric acid, whereupon the temperature rises to 53° C. To this solution are then added dropwise 55.5 g of epichlorohydrin in the course of 40 minutes, the temperature being held between 65° and 70° C. After completion of the addition, the reaction mixture is stirred at 68° C. for a further 5½ hours. The epoxide content after this time is zero. The reaction mixture is evaporated to dryness to heated to 95° to 98° C. There are then added 20 g of a dye of the formula

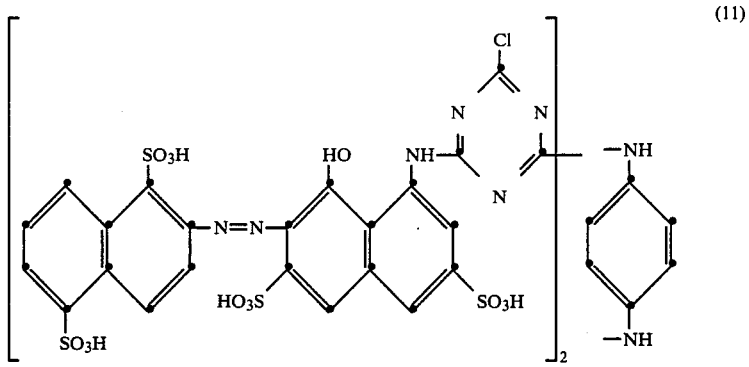

(11)

thus obtain 137 g of 1-(3'-chloro-2'-hydroxypropylaminopropyl)3-(3'-chloro-2'-hydroxypropyl)-2-phenyl-imidazolium sulfate.

EXAMPLE 4

38.9 g of 1-(3-aminopropyl)-2-heptadecylimidazole are mixed with 145 g of water and 5.1 g of 96% sulfuric acid, and the mixture is heated to 60° C. There are then added dropwise 18.5 g of epichlorohydrin in the course of 25 minutes. After the addition has been completed, the reaction mixture is stirred at 78° C. for 1½ hours. The epoxide content after this time is zero. The yield is 62 g of 1-(3'-chloro-2'-hydroxypropylaminopropyl)-3-(3'-chloro-2'-hydroxypropyl)-2-heptadecyl-imidazolium sulfate.

EXAMPLE 5

25 g of 1-(3-aminopropyl)-imidazole are dissolved in 70.3 g of water and 10.2 g of 96% sulfuric acid, whereupon the temperature rises to 59° C. There are then added dropwise in the course of 30 minutes 55.5 g of epichlorohydrin, the temperature being maintained at between 65° and 70° C. After completion of the dropwise addition, the reaction mixture is held at 70° C. for a further 1 hour. The epoxide content after this time is zero. The reaction mixture is subsequently evaporated to dryness to thus obtain 90 g of 1-[di-(3'-chloro-2'-hydroxypropyl)-aminopropyl]-3-(3'-chloro-2'-hydroxypropyl)-imidazolium sulfate.

APPLICATION EXAMPLES

Example 1

In a cheese dyeing machine, 500 g of cotton yarn are wetted into 5 liters of water, whereupon the liquor is and 400 g of sodium sulfate. The temperature is lowered to 80° C., and 10 ml of a 30% aqueous sodium hydroxide solution and 25 g of sodium carbonate are added. The liquor is cooled further to 40° C., and there are subsequently added 60 ml of the 30% sodium hydroxide solution and 50 g of the 1-(3'-chloro-2'-hydroxypropylaminopropyl)-3-(3'-chloro-2'-hydroxypropyl)-imidazolium sulfate produced according to Example 1. The textile material is afterwards treated at 40° C. for 60 minutes, and then rinsed and dried.

A level, intensely coloured, red dyeing having an increased dye yield and excellent fastness to wet processing is obtained. The ISO-C2S washing is clearly improved.

Example 2

In a short-liquor jet machine, 100 g of cotton fabric are wetted with 800 g of water. The bath is then heated to 40° C., and 3 g of a direct dye of the formula

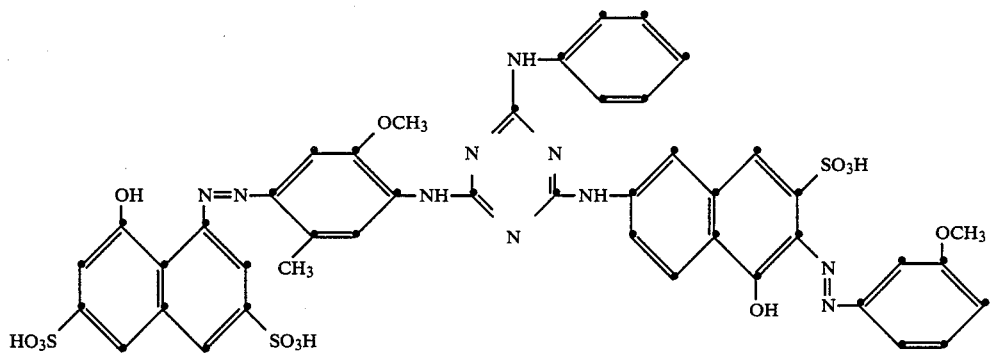

(12)

and 48 g of sodium sulfate are added. There are introduced after 10 minutes, at the same temperature, 9.6 g of a 30% aqueous sodium hydroxide solution and 8 g of the 1-(3'-chloro-2'-hydroxypropylaminopropyl)-3-(3'-chloro-2'-hydroxypropyl)-imidazolium sulfate produced according to Example 1. The fabric is subsequently treated at 40° C. for 60 minutes, and afterwards rinsed and dried.

A level, intensely coloured, red dyeing having a 50% increase in dye yield is obtained. The ISO-C2S washing test gives the rating 4.

Example 3

A cotton fabric is impregnated on a padding machine with a liquor containing per liter:
60 g of the dye of the formula

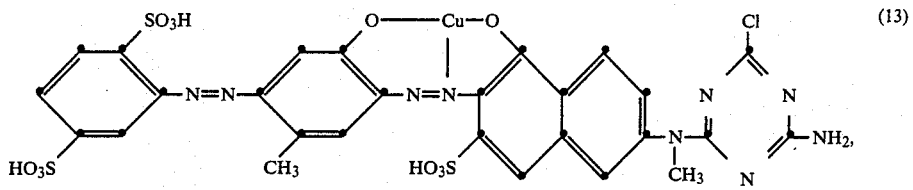

100 g of urea,
35 g of the 1-(3'-chloro-2'-hydroxypropylamino-propyl)-3-(3'-chloro-2'-hydroxypropyl)-imidazolium sulfate produced according to Example 1,
20 g of sodium carbonate, and
3 g of the sodium salt of 3-nitrobenzenesulfonic acid.

The liquor pick-up amounts to 80%. The fabric is afterwards rolled up and is stored for 18 hours at room temperature. The fabric is subsequently washed hot and then cold and finally dried.

An intensely coloured, level blue dyeing having a 20% improvement in dye yield is obtained. After storage in an atmosphere saturated with steam for 3 days at 60° C., the dyeing has caused no staining of the accompanying fabric (hydrolysis test before the ISO-C2S washing test). The ISO-C2S washing test gives a rating of 4 also after the hydrolysis test.

fastness to wet processing of the dyeing is excellent. In the ISO-C2S washing test and in the fastness to moist ironing test, the accompanying fabric is virtually unstained.

Example 5

A dyeing, which has been produced on cotton tricot with 6% of the dye of the formula (11), is padded with a liquor containing per liter:
26 g of the 1-(3'-chloro-2'-hydroxypropylamino-propyl)-3-(3'-chloro-2'-hydroxypropyl)-imidazolium sulfate obtained according to Example 1, and
15 ml of a 30% sodium hydroxide solution. The liquor pick-up is 85%. The material is afterwards dried at 90° C., and then treated for 3 minutes at 140° C. for the purpose of fixing.

After a hydrolysis test, the material gives the rating 4 in the ISO-C2S washing test.

Example 6

A dyeing produced in the conventional manner with 5% of a dye of the formula

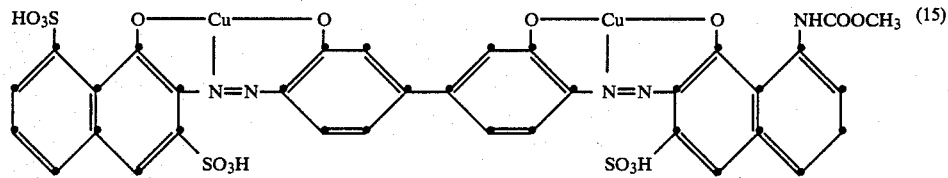

Example 4

A cotton tricot is padded with a liquor containing per liter:
12 g of the dye of the formula

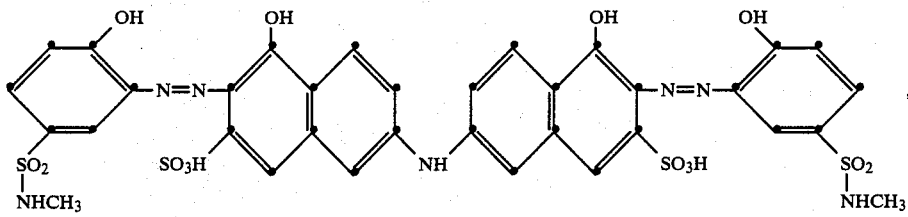

100 g of urea,
20 g of a 30% sodium hydroxide solution, and
26 g of the 1-(3'-chloro-2'hydroxypropylamino-propyl)-3-(3'-chloro-2'-hydroxypropyl)-imidazolium sulfate produced according to Example 1.

The material is afterwards rolled up, hermetically packed, and stored for 20 hours at room temperature. The textile material is subsequently rinsed and dried. An intensely coloured violet dyeing is obtained, the increase in dye yield of which is 100%. Furthermore, the is aftertreated in the manner described in Example 5. The tests with respect to the ISO-C2S washing and fastness to moist ironing show (in contrast to tests of a dyeing subsequently fixed conventionally) no staining of the accompanying fabric.

Example 7

Before being dyed, a cotton fabric is padded with a liquor containing per liter:
26 g of the 1-(3'-chloro-2'-hydroxypropylamino-propyl)-3-(3'-chloro-2'-hydroxypropyl)-imidazolium sulfate produced according to Example 1, and
25 ml of a 30% sodium hydroxide solution.

The material is afterwards dryed at 90° C. and is then subjected to thermosol fixation at 140° C. for 3 minutes.

1 kg of the pretreated fabric is wetted into 30 liters of water at 25° C., whereupon there are added 30 g of the dye of the formula

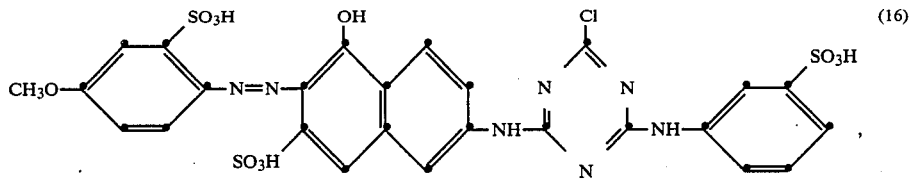

600 g of sodium carbonate and 90 ml of a 30% sodium hydroxide solution. The dye liquor is heated in the course of 40 minutes to 80° C., and is held for 60 minutes at this temperature. The dyed fabric is subsequently rinsed hot and then cold and finally dried.

The dye yield is improved by 60% as a result of the pretreatment of the material with the imidazolium salt. The dyeing moreover exhibits excellent fastness to wet processing.

Example 8

Bleached cotton terry is printed on a roller printing machine with 1 kg of a printing paste of the following composition:
400 g of a 5% alginate thickener,
100 g of urea,
50 g of a dye of the formula

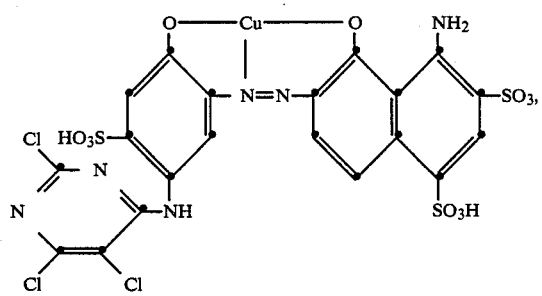

10 g of m-nitrobenzenesulfonic acid (sodium salt),
60 g of a 30% sodium carbonate solution, and
380 g of water,
the printing being carried out in such a manner that 3 cm printed stripes alternate with 3 cm unprinted stripes. The material is then dried, steamed for 8 minutes at 101° C., rinsed, soaped at the boil and afterwards dried. The printed material is subsequently padded with a liquor containing per liter:
23 g of the 1-(3'-chloro-2'-hydroxypropylaminopropyl)-3-(3'-chloro-2'-hydroxypropyl)-imidazolium sufate produced according to Example 1, and
30 ml of a 30% sodium hydroxide solution.
The liquor pick-up is 85%. The material is then dried at 80° C., and treated at 140° C. for 3 minutes. The material is finally rinsed and dried. The fastness to wet processing, particularly in the ISO-C2S washing test, and the fastness to moist ironing of the coloured printing are clearly improved by this aftertreatment with the imidazolium salt, also after a hydrolysis test.

Similarly good effects are obtained with the use of 23 g of each of the imidazolium salts produced according to Examples 2 to 5.

What is claimed is:

1. A 1-aminoalkyl-imidazolium compound which

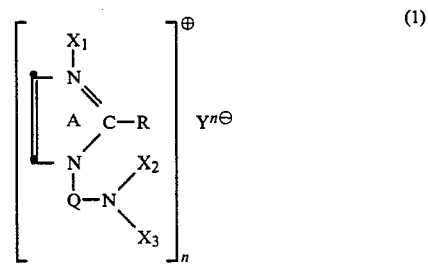

contains in the 3-position and on the terminal amino group fibre-reactive groupings which have been formed by the addition of an epihalohydrin.

2. An imidazolium compound of the formula $$\left[ \begin{array}{c} X_1 \\ | \\ N \\ A \diagdown C-R \\ N \diagup X_2 \\ | \\ Q-N \diagdown X_3 \end{array} \right]_n^{\oplus} Y^{n\ominus} \quad (1)$$

wherein
$X_1$ and $X_2$ independently of one another are each the group

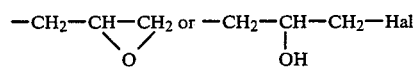

$X_3$ is hydrogen, lower alkyl,

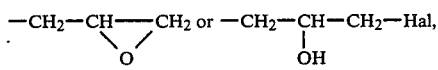

Hal is halogen,
Q is alkylene having 2 to 4 carbon atoms,
R is hydrogen, phenyl or an aliphatic $C_1$-$C_{23}$-radical,
n is 1 or 2, and
$Y^{\ominus}$ is an anion of a strong inorganic or organic acid, and wherein the imidazole ring A is furhter unsubstituted, or is further substituted by lower alkyl which is unsubstituted or substituted by halogen, hydroxyl or cyano.

3. An imidazolium compound according to claim 2, wherein, in the formula (1), $X_1$ and $X_2$ are the halohydrin groups of the formula

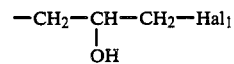

wherein $Hal_1$ is bromine or chlorine.

4. An imidazolium compound according to claim 2, wherein $X_3$ in the formula (1) is hydrogen.

5. An imidazolium compound according to claim 2, wherein Q in the formula (1) is the propylene group $-CH_2-CH_2-CH_2-$.

6. An imidazolium compound according to claim 2 of the formula

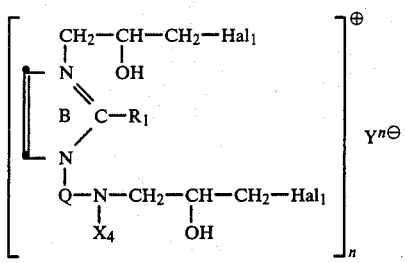 (2)

wherein
Q is alkylene having 2 to 4 carbon atoms,
$R_1$ is hydrogen, phenyl or alkyl having 1 to 17 carbon atoms,
$X_4$ is hydrogen or

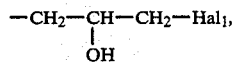

and
$Hal_1$ is bromine or chlorine, n is 1 or 2, and
$Y^\ominus$ is an anion of a strong inorganic or organic acid, and the ring B is further unsubstituted or further substituted by methyl or ethyl.

7. An imidazolium compound according to claim 2, of the formula

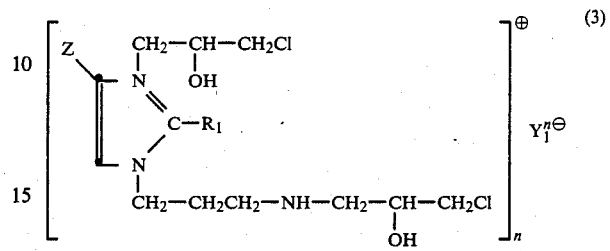 (3)

wherein
$R_1$ is hydrogen, phenyl or alkyl having 1 to 17 carbon atoms,
Z is hydrogen or methyl,
n is 1 or 2, and
$Y_1{}^{n\ominus}$ is the chloride or sulfate ion.

8. 1-(3'-chloro-2'-hydroxypropylaminopropyl)-3-(3'-chloro-2'-hydroxypropyl)-imidazolium chloride or sulfate.

* * * * *